United States Patent [19]

Shively

[11] 4,409,205
[45] Oct. 11, 1983

[54] OPHTHALMIC SOLUTION

[75] Inventor: Charles D. Shively, Highland Park, Ill.

[73] Assignee: Cooper Laboratories, Inc., Palo Alto, Calif.

[21] Appl. No.: 225,853

[22] Filed: Jan. 16, 1981

Related U.S. Application Data

[63] Continuation-in-part of Ser. No. 17,372, Mar. 5, 1979, abandoned.

[51] Int. Cl.$^3$ ............................................... A61K 31/74
[52] U.S. Cl. ...................................... 424/78; 424/361
[58] Field of Search ................................. 424/78, 361

[56] References Cited

U.S. PATENT DOCUMENTS

| | | | |
|---|---|---|---|
| 3,311,577 | 3/1967 | Rankin | 424/78 |
| 3,843,782 | 10/1974 | Krezanoski et al. | 424/78 |
| 3,856,919 | 12/1974 | Rankin | 424/80 |
| 3,920,810 | 11/1975 | Rankin | 424/80 |
| 3,927,205 | 12/1975 | Ohno et al. | 424/78 |
| 4,003,991 | 1/1977 | Krohn et al. | 424/81 |
| 4,039,662 | 8/1977 | Hecht et al. | 424/180 |

FOREIGN PATENT DOCUMENTS 1090492 11/1967 United Kingdom ................. 424/78

*Primary Examiner*—Douglas W. Robinson
*Attorney, Agent, or Firm*—Thomas R. Boland

[57] ABSTRACT

An ophthalmic aqueous solution having an ionic salt ion content within the range 0.01% to 7.5% expressed as sodium chloride equivalents and comprising a non-ionic synthetic polymer such as polyvinyl alcohol and/or polyethylene glycol, and a non-ionic tonicity adjusting agent. The solution is effective in treating "dry eye" conditions by causing a normalization of irregularly structured tears and at least retarding the precipitation of potein-like substances from the aqueous layers thereof.

9 Claims, No Drawings

OPHTHALMIC SOLUTION

CROSS-REFERENCE TO CO-PENDING APPLICATION

This is a continuation-in-part of U.S. Ser. No. 17,372, filed Mar. 5, 1979 now abandoned.

BACKGROUND OF THE INVENTION

1. Field of the Invention

This invention relates to a unique ophthalmic solution which is designed for general use in mammalian eyes but which is especially adapted for use in normalizing irregularly structured tear films in the eyes of humans and domestic animals. Thus, while the ophthalmic solution of this invention may be utilized generally as a carrier for ophthalmic medicaments, it will also be particularly useful when employed alone in the treatment of certain ophthalmologic conditions. For example, the present ophthalmic solution can serve as an artificial tear substance when administered to the eyes of patients whose tears are incorrectly structured and characterized by high sodium or potassium content as well as an aqueous volume significantly reduced from that of normal tears. The ophthalmic solution described herein is also effective as a lubricating agent for the eye following traumatic injury, exposure keratitis or surgery. In addition, this ophthalmic solution may be used to strengthen the tear films in the eyes of those who wear either hard or soft contact lenses.

2. Description of the Prior Art

Ophthalmic solutions have been previously developed for treating "dry eye" syndrome or for use as lubricating and cushioning agents for an eye subjected to traumatic injury or surgery. Such solutions have generally been isotonic, buffered to a required pH and contain various synthetic polymers as essential additives for improved viscosity and longer retention in the eye.

U.S. Pat. No. 3,767,788 to Rankin for example discloses one such solution which includes as an essential additive a high molecular weight ethylene oxide polyether, such as polyethylene oxide, along with other optional substituents, e.g. polyethylene glycol as a humectant, and various biocides and preservatives.

U.S. Pat. No. 3,907,985 to Rankin discloses another ophthalmic solution in a similar vein which is said to be effective in treating eye conditions such as dry eye but includes polystyrene sulfonate as an essential ingredient.

U.S. Pat. No. 4,039,662 to Hecht et al. describes an ophthalmic solution containing a particular polysaccharide and benzalkonium chloride which together apparently produce a synergistic effect and provide a synthetic tear film component which imparts a mucin-like layer to the cornea.

Since it has been commonly accepted in the art that isotonic levels of monovalent cation containing salts, principally sodium and potassium ions, are necessary to maintain tear films in a normal state, and thus prevent ocular discomfort or damage to the cornea and surrounding eye tissues, there is a clear indication in the abovementioned references and in other disclosures of the prior art that suitable ophthalmic solutions should incorporate relatively high levels of sodium ions, for example, to provide such solutions with a level of tonicity synonymous with body fluids. As will be described in greater detail below, it has now been discovered that an ophthalmic solution will be much more effective in restoring an irregularly structured tear film to its normal state if the amount of cationic salts, i.e. sodium salts, in the solution are controlled to a minimum level.

SUMMARY OF THE DISCLOSURE

In its broadest sense, the present invention provides an ophthalmic solution having an ionic salt ion concentration within the range of from about 0.01% to about 0.75%, expressed as sodium chloride equivalents, which when topically administered to the eye of a patient afflicted with a condition characterized by an irregularly structured tear film, will be effective in returning that tear film to its precondition normalcy.

More specifically, the ophthalmic solution of this invention is an aqueous solution comprising an ophthalmically acceptable, non-ionic synthetic polymer having a molecular weight between about 300 to about 250,000, such as polyvinyl alcohol or polyethylene glycol, along with a non-ionic, non-charged, tonicity adjusting agent which, for example, may be selected from the group consisting of mannitol, sorbitol, dextrose, sucrose, urea and glycerol. The solution may additionally include biocides and/or preservatives as optional ingredients and these may be selected from those commercially available substances which are commonly used in eye treating solutions, such as, for example, benzalkonium chloride or thimerosal sodium. Suitable chelating agents, such as di-, tri- or tetra-sodium ethylene diamine, preferably disodium edetate, may also be included in the solution. The pH of the solution may be adjusted as desired, but it will generally range from about 4.5 to 8.5, preferably about 5.0 to about 7.0. Compatible, conventional buffers, such as weak acids or weak bases, may be used to adjust the pH and their selection and concentration may be correlated with certain preservatives, such as trisodium edetate, to achieve the desired level. While the viscosity of the solution of this invention may vary, depending on the molecular weight of the selected non-ionic synthetic polymer and whether or not optional viscosity building agents are added to the solution, it will generally fall within the range of between about 1 cps and about 150 cps, preferably from about 2 cps to about 80 cps.

Thus, it is in keeping with the overall concept of this invention that its principal object is to provide an ophthalmic solution which when topically applied to an eye afflicted with an abnormal ophthalmologic condition at least in part characterized by an irregularly structured tear film, will cause the reestablishment of that tear film to its pre-abnormal condition state, i.e., the present solution will cause the various layers of the tear film to assume relative dimensions which at least approximate those of its pre-condition structure.

It is another object of the invention to provide an ophthalmic solution which when applied to the eye of a human will establish a tonicity therein which at least retards the precipitation of dehydrated protein-like substances in the tears and indeed promotes the resolubilization of such protein-like substances which may have emerged previously from solution.

It is yet another object of the invention to provide an ophthalmic solution which will serve as an artificial tear additive which is effective in the treatment of "dry eye" syndrome.

It is an additional object of the invention to provide an ophthalmic solution which will be useful in reducing minor eye irritations commonly associated with the wearing of hard and soft contact lenses, especially when such lenses are worn by individuals whose eyes contain irregularly structured tear films.

It is a further object of this invention to provide a unique carrier for ophthalmic medicaments.

The manner in which these and other objects of the present invention are obtained will be more concisely demonstrated, and a greater appreciation of the invention realized, from the following detailed description and accompanying claims.

DESCRIPTION OF THE INVENTION

The present invention comprises an ophthalmic aqueous solution whose ionic salt ion content is limited to the lowest possible amount, i.e. within the range of 0.01% to about 0.75% expressed as sodium chloride equivalents. Thus, the solution will preferably contain no mono-, di-, or trivalent cationic tonicity adjusting salts. The solution comprises as essential ingredients an ophthalmically acceptable, water-soluble, non-ionic synthetic polymer having a molecular weight within the range of 300 to 250,000, and a non-charged, non-ionic tonicity adjusting agent.

It is, of course, well known that a diseased eye, or one which has been traumatically injured or subjected to surgery, will usually have tears which are irregularly structured, and this is especially true in the case of those afflicted with "dry eye" syndrome. The essential ingredients of this invention work together to stabilize the mucin layer of such tears and to mitigate against an increased viscosity in the aqueous layer of the tears while promoting a reestablishment of a tear structure wherein the respective layers have dimensions at least approximating a normal state.

The exact percentage of the non-ionic synthetic polymer used in the solution will depend on the molecular weight of the selected polymer. However, it is intended that, absent the presence of additional viscosity building agents, the ophthalmic solution will generally have a viscosity between about 1 to about 10 cps, preferably about 2 cps to about 8 cps at 23° C. For example, polyvinyl alcohol and polyethylene glycol are among those non-ionic polymeric substances which are especially preferred for use in this invention. When polyvinyl alcohol is added to the solution, it will be present in a concentration of from about 0.1% to about 5%, preferably from about 0.25% to about 2%, whereas when polyethylene glycol is utilized it will comprise from about 0.25% to about 3% of the solution. Such polymers are commercially available and their composition well known to those skilled in the art.

The non-ionic tonicity adjusting agent has an important function in the invention since it provides a tonicity in the eye which at least retards, and in most cases prevents entirely, the precipitation of protein-like substances from the aqueous layer of the tears, and promotes the resolubilization of those protein-like substances which have emerged from the aqueous layer prior to treatment with the solution. It is not possible to achieve this effect when using previously known ophthalmic solutions containing relatively high amounts of ionic salt ions, e.g. sodium and/or potassium ions, because such solutions frustrate the establishment of a stabilizing tonicity in the eye and predispose the aforementioned precipitation of protein-like substances. Suitable tonicity adjusting agents may be selected, for example, from the group consisting of mannitol, sorbitol, dextrose, sucrose, urea and glycerol. Regardless of which tonicity adjusting agent is selected, it will be present in the solution in a concentration of from about 0.5% to about 5%, preferably from about 0.25% to about 3.5%.

In those instances where the solution is intended for use in connection with contact lenses, thereby contributing protection against the minor irritations associated with the wearing of such lenses, viscosity increasing agents may also be added to the formulation. Such viscosity increasing agents may include cellulosic polymers such as hydroxyethylcellulose, hydroxypropylcellulose, methylcellulose, hydroxypropylmethylcellulose and carboxymethylcellulose, as well as polymeric polyalkylene glycols and oxides, and polyoxypropylene-polyoxyethylene block copolymers. However, it should be understood that even in this specialized application the viscosity of the solution will not be greater than about 150 cps at 23° C. For most artificial tear usages, the viscosity of this solution will be low when compared to other commercially available polymer-containing ophthalmic solutions. All references to viscosity in this disclosure are related to measurement on a Wells-Brookfield Microviscometer (cone and plate) Model LVT.

Preferably, the ophthalmic solution contains a compatible preservative or biocide in an amount effective to afford protection against bacterial contamination. Any conventional preservative system may be used. Quaternary germicides, particularly benzalkonium chloride, are presently preferred. Benzalkonium chloride is an alkyl substituted dimethylbenzylammonium chloride in which the alkyl substituents comprise a mixture of $C_8$ to $C_{18}$ alkyl radicals. Still other useful preservatives or biocides are thimerosol sodium, phenylmercuric acetate, methyl, ethyl and propyl para-aminobenzoic acid esters, and the like. The preservatives can be used individually or in combination. They are used in effective amount to afford protection against contamination. For example, amounts of from about 0.001% to about 0.03% by weight of a quaternary or organic mercurial germicide are known to be effective and can be used in the present invention. It is also generally desirable to include a chelating agent in the solution to enhance the preservation effect of benzalkonium chloride, for example. Suitable chelating agents include di-, tri-, or tetrasodium ethylene diamine tetraacetate, also known as edetates, although disodium edetate is the preferred substance. Such a chelating agent will be added in an amount ranging between 0.025% to 0.1% w/v.

The pH of the solution may be adjusted as desired by means well known in the art. That is to say, weak acids or weak bases, and buffering systems commonly employed in ophthalmic solutions may be utilized for this purpose. Generally, the pH of the present solutions may range from about 4.5 to 8.5. However, typically the pH of the ophthalmic solutions described herein is from about 5 to about 8, and especially from about 6 to about 7.5.

The ophthalmic solutions described herein may also be used as a carrier for one or more pharmaceutically active materials, preferably selected from those which are water-soluble. Such compositions may be easily prepared by conventional techniques, such as by a simple mixing procedure. In any event, the drug or medicament utilized will be selected on the basis of the treatment indicated for the patient and will be employed in pharmacological amounts. Exemplary drugs which may be used in connection with the ophthalmic solution of this invention are pilocarpine HCl for glaucoma, phenylephrine for red eyes and dexamethasone or fluoromethalone for inflammatory ocular conditions. Various anti-microbial pharmaceuticals for treatment of fungal and viral diseases of mucous membranes may be used, such as clofazimine, pimaricin, neomycin sulfate, chloramphenicol, bacitracin, sulfacetamide, gentamycin, polymixin B sulfate, and the like. The composition will, of course, be applied to the patient's eye in sufficient dosage to deliver a pharmacologically effective amount to the treatment area.

Essentially any conventional solution forming technique may be utilized in preparing the aqueous ophthalmic solutions of this invention, and when so formed they may be applied to the eyes by any known means. Preferably, application will be in drop form in the manner typically used, for example, to apply eye drops. Thus, the normal squeeze-type liquid drop application devices are perfectly suitable for use in applying the ophthalmic solutions of this invention to an eye intended for treatment.

For a clearer understanding of the invention, specific examples of it are set forth below. These examples are merely illustrative and are not to be understood as limiting the scope and underlying principles of the invention in any way. All parts and percentages referred to in this specification and the appended claims are by weight in terms of unit volume of solution unless otherwise specifically indicated. Thus, a benzalkonium chloride content of 0.1% in the solution is equivalent to one gram of benzalkonium chloride per liter of solution.

EXAMPLE I

An ophthalmic solution according to this invention was prepared with the following formulation:

| Ingredient | Percent (w/v) |
|---|---|
| Polyvinyl alcohol U.S.P.[1] | 1.0% |
| Polyethylene glycol 6000[2] | 2.0% |
| Dextrose | 3.3% |
| Benzalkonium chloride | 0.01% |
| Disodium edetate | 0.03% |
| Water, sufficient to make | 100% |

[1] Monsanto 20-30 B.P.
[2] Molecular weight of 6000

The solid ingredients are weighed, separately mixed and thereafter added to purified water with stirring. Benzalkonium chloride is then added and mixing completed. The solution is then asceptically filtered and dispensed into presterilized bottles for clinical testing.

In one clinical study the above formulation was applied to the eyes of 101 patients who were under physician care, and diagnosed as being variously afflicted with keratoconjunctivitis sicca, dry eyes of various corneal problems. As a result, it was demonstrated that the above ophthalmic solution provided substantial improvement in seven key symptom areas associated with the ocular irritation syndromes. Table 1, below, presents the key symptoms and those individual response percentages which reflected an improvement in the symptom (less of a problem) and a worsening of the symptom (more of a problem).

TABLE 1

| | Clinical Impression | | | |
|---|---|---|---|---|
| Symptom | Patients with Complaint | More of a Problem | No Change | Less of a Problem |
| Blurred Vision | n = 31 | 2 (6%) | — — | 29 (94%) |
| Photophobia | n = 26 | 2 (8%) | — — | 24 (92%) |
| Burning | n = 74 | 19 (26%) | 4 (5%) | 51 (69%) |
| Foreign Body Sensation | n = 44 | 12 (23%) | 9 (17%) | 32 (60%) |
| Itching | n = 34 | 6 (18%) | 6 (18%) | 22 (65%) |
| Tearing | n = 33 | — — | — — | 33 (100%) |
| Lid Crusting | n = 44 | 6 (14%) | 4 (9%) | 34 (77%) |

In another study on 16 patients during which the patients were examined a minimum of three office visits each, a high percentage of the patients showed improvements in clinical symptoms and slit lamp examinations. The symptoms studied and the results obtained in this study using the above-noted formulation are presented in Table 2 below.

TABLE 2

| | Open Label Clinical Observations | | | | | | | |
|---|---|---|---|---|---|---|---|---|
| Symptoms | Occurrences | 2 or 3+ Worsened | 1+ Worsened | No Change | 1+ Improvement | 2+ Improvement | 3+ Improvement | Showed Improvement |
| Foreign Body Sensation | n = 42 | 3 (7%) | 4 (10%) | 7 (17%) | 19 (45%) | 5 (12%) | 4 (10%) | 67% |
| Blurred Vision | n = 10 | 2 (20%) | — — | 1 (10%) | 5 (50%) | — — | 2 (20%) | 70% |
| Photophobia | n = 6 | — — | — — | 2 (33.3%) | 2 (33.3%) | 2 (33.3%) | — — | 67% |
| Lid Crusting | n = 18 | — — | — — | 2 (11%) | 4 (22%) | 12 (67%) | — — | 89% |
| Burning | n = 34 | — — | — — | 3 (9%) | 19 (56%) | 8 (24%) | 4 (12%) | 92% |
| Itching | n = 27 | — — | 4 (15%) | 3 (11%) | 14 (52%) | 3 (11%) | 3 (11%) | 74% |
| Tearing | n = 14 | — — | — — | 3 (21%) | 10 (71%) | 1 (7%) | — — | 78% |
| Slit Lamp Exam | | | | | | | | |
| Debris in Tear Film | n = 29 | 2 (7%) | 5 (17%) | 12 (41%) | 3 (10%) | 5 (17%) | 2 (7%) | 34% |
| Viscous Tear Film | n = 31 | — — | 2 (6%) | 9 (29%) | 15 (48%) | 5 (16%) | — — | 64% |
| Diminished Marginal Tear Strip | n = 37 | — — | 1 (3%) | 13 (35%) | 16 (43%) | 7 (19%) | — — | 62% |
| Fluorescein Stain-Cornea | n = 32 | 1 (3%) | 5 (16%) | 7 (22%) | 13 (41%) | 4 (13%) | 2 (6%) | 60% |

The final clinical study performed on the Example I formulation compared its use with a currently marketed composition for use as an artificial tear in contact lens wear. Twenty-seven (27) contact lens wearers (19 hard contact lens wearers [HCL] and 8 soft contact lens wearers [SCL]) were selected to evaluate the addition of the new composition eyedrop as a contact lens artificial tear wetting agent. Of this group ten (10) patients were aphakic or had corneal transplants, whereas fourteen (14) patients were phakic. Three patients did not complete the study. The results of this study, presented in Table 3, indicate an overall preference for the ophthalmic solution defined above (Formulation HT) over a currently marketed composition (Formulation LT). The symbol (NP) indicates no preference.

TABLE 3

A. Preference statements by aphakic or post-keratoplasty patients wearing contact lenses and trying Formulation HT and Formulation LT

|     | HT | LT | NP | TOTAL |
|-----|----|----|----|-------|
| HCL | 6  | 1  | 0  | 7     |
| SCL | 1  | 1  | 1  | 3     |
|     | 7  | 2  | 1  | 10    |

B. Preference statements by phakic patients.

|     | HT | LT | NP | TOTAL |
|-----|----|----|----|-------|
| HCL | 5  | 2  | 2  | 9     |
| SCL | 5  | 0  | 0  | 5     |
|     | 10 | 2  | 2  | 14    |

C. Preference statements by hard and soft contact lens wearers, irrespective of other ocular conditions.

|     | HT | LT | NP | TOTAL |
|-----|----|----|----|-------|
| HCL | 11 | 3  | 2  | 16    |
| SCL | 6  | 1  | 1  | 8     |
|     | 17 | 4  | 3  | 24    |

EXAMPLE II

This example illustrates the difference in tear break-up time between the present invention and a prior art solution, i.e., namely a solution covered by the disclosure in U.S. Pat. No. 3,843,782. A tear break-up time study is a technique for measuring tear quality in which break-up time ("BUT") is defined as the interval between a complete blink and the appearance of the first randomly distributed dry spot. BUT has been demonstrated to be abnormally rapid in dry eye states as a result of decreased tear film stability, and the addition of an artificial tear solution into the conjunctival sac has been shown to affect the BUT in such a way that a "definite, reproduceable alteration in BUT occurs..." (Lemp., M.A., 1975).

Ten normal subjects (20 eyes) with normal tear break-up time participated in the study and data from each eye were considered individually. Base line BUT measurements were obtained by applying a slightly moistened fluorosine strip to the inferior temporal bulbar conjunctive and the subject was instructed to blink several times in order to distribute the fluorocein. The patient was again instructed to blink and then to keep eyes open and look straight ahead. A stop watch was started after the blink and using the broad beam of the slit lamp the tear film was scanned, to time formation of a dry spot. The measurement was repeated twice using the average of the three measurements as BUT for that eye. The number and location of dry spots were observed and recorded.

The test measurements were obtained in a procedure which initially involved placing one drop of a test solution in the inferior palpebral conjunctiva and the subject was instructed to blink in order to distribute the drop. The above-mentioned procedure for conducting the baseline BUT measurements was repeated and BUT measurements taken at 5 minutes, 10 minutes, 15 minutes and at 15 minute intervals thereafter until 45 minutes after instillation of the eye drop.

The test solutions were administered in a double masked cross-over fashion into both eyes of each subject. There were two test sessions for each subject administered a minimum of 25 hours apart. The order of testing was as follows ("PAS"=Prior Art Solution; "IS"=Invention Solution):

TABLE 4

| Subject # | Testing Session 1 | Testing Session 2 |
|-----------|-------------------|-------------------|
| 1         | PAS               | IS                |
| 2         | IS                | PAS               |
| 3         | IS                | PAS               |
| 4         | PAS               | IS                |
| 5         | PAS               | IS                |
| 6         | IS                | PAS               |
| 7         | IS                | PAS               |
| 8         | PAS               | IS                |
| 9         | PAS               | IS                |
| 10        | IS                | PAS               |

Table 5 presents the formulation of the two test solutions used in the study.

TABLE 5

| Present Invention | |
|---|---|
| PVA (20–30) | 1.0% |
| PEG 6000 | 2.0% |
| Dextrose | 3.3% |
| DSEDTA | 0.03% |
| BAC | 0.1% = 10% xs |
| pH | 7.0 |
| H$_2$O | Q.S. |
| Vicosity | 1.56 cps |
| Tonicity | 226 milliosmoles |
| (0.7% sodium chloride equivalents) | |

| Prior Art | |
|---|---|
| HEC (Natrasol 250 MR) | 0.135% |
| PVA (20–30) | 0.019% |
| Sodium Bicarbonate | 0.25% |
| Sodium Chloride | 1.0% |
| Potassium Chloride | 0.2% |
| TSEDTA | 0.025% |
| BAC | 0.005% |
| H$_2$O | Q.S. |
| Vicosity | 2.8 cps |
| Tonicity | 429 milliosmoles |
| (1.35% sodium chloride equivalents) | |

The mean tear BUT measurements as measured in seconds for both solutions are presented in Table 6.

TABLE 6

| Time Interval | Present Invention | Prior Art |
|---|---|---|
| Baseline | 20.9 seconds | 23.7 seconds |
| Time 0 - Drop Instilled | - - - - - - - - - - - - - - - | |
| 5 minutes | 16.9 | 17.5 |
| 10 minutes | 25.7 | 14.9 |
| 15 minutes | 28.7 | 15.3 |
| 30 minutes | 22.1 | 14.3 |
| 45 minutes | 27.1 | 20.9 |

The above data illustrates that of the 20 eyes treated with the solution of this invention, with the exception of the first measurement at 5 minutes, the mean break-up time was elevated over the mean baseline measurement. The 5 minute measurement was 3.9 seconds or 19% less than the baseline.

The mean tear film BUT for eyes treated with the prior art solution was reduced for all measurements and the mean 5 minute level in this sample was 6.1 seconds less or a 26% decrease.

The maximum difference between the two test solutions was noted at 15 minutes where the claimed solution had extended the tear BUT by 8 seconds or 39% over baseline while the prior art solution level was 8.5 seconds or 36% below baseline.

At the end of the 45 minute test period, the tear BUT level for the solution of the present invention remained elevated while the prior art solution curve did not yet return to the baseline level.

These results clearly support the conclusion that the solution of the present invention caused a unique and unexpected extension of tear break-up time and produced results which are significantly better than those realized in using the prior art solution.

EXAMPLE III

Results similar to those described above in connection with Example I will be achieved with the following formulation:

| Ingredient | Percent (w/v) |
|---|---|
| Polyvinyl alcohol U.S.P.[1] | 0.25% |
| Polyethylene glycol 6000[2] | 2.0% |
| Dextrose | 3.3% |
| Benzalkonium chloride | 0.01% |
| Disodium edetate | 0.03% |
| Water, sufficient to make | 100% |

[1]Monsanto 20-30 B.P.
[2]Molecular weight of 6000

EXAMPLE IV

The following formulation was prepared according to the method described in Example I, in order to test the reaction of contact lens wearers who require an ophthalmic solution to wet, clean and soak their contact lenses:

| Ingredient | Percent (w/v) |
|---|---|
| Polyvinyl alcohol U.S.P.[1] | 0.25% |
| Polyethylene glycol 6000[2] | 0.25% |
| Pluronic F-127[3] | 0.25% |
| Hydroxyethylcellulose 250 MR | 0.4% |
| Dextrose | 5.0% |
| Benzalkonium chloride | 0.01% |
| Disodium edetate | 0.03% |
| Water, sufficient to make | 100% |

[1]Monsanto 20-30 B.P.
[2]Molecular weight of 6000
[3]BASF Wyandotte Corporation Subjective responses from the tested individuals indicated a strong preference for the above defined composition as compared to other currently used contact lens solutions used for wetting, cleaning and storing lenses. Of particular importance was the comfort associated with use of the composition as a lens cushioning and rewetting solution while reducing normal vision blurring and lid crusting.

It should be understood that this invention may be embodied in other specific forms without departing from its spirit or essential characteristics. Accordingly, the present embodiments are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. An ophthalmic solution for use in normalizing irregularly structured tear films in mammalian eyes having an ionic salt ion content within the range of from about 0.01% to about 0.75% expressed as sodium chloride equivalents, and a viscosity within the range of from about 1 cps to 150 cps at 23° C., comprising an aqueous solution of a water soluble non-ionic synthetic polymer having a molecular weight within the range of from about 300 to about 250,000 and selected from the group consisting of polyvinyl alcohol, polyethylene glycol and mixtures thereof, and from about 0.1 to about 5.0% of a non-ionic tonicity adjusting agent selected from the group consisting of mannitol, sorbitol, dextrose, sucrose, urea, glycerol and mixtures thereof.

2. An ophthalmic solution according to claim 1 wherein the non-ionic synthetic polymer is polyvinyl alcohol, in an amount of from about 0.1% to about 5.0%.

3. An ophthalmic solution according to claim 1 wherein the non-ionic synthetic polymer is polyethylene glycol in an amount of from about 0.25% to about 3.5%.

4. An ophthalmic solution according to claims 1 or 2 or 3 further comprising a viscosity increasing agent.

5. An ophthalmic solution according to claim 4 wherein said viscosity increasing agent is selected from the group consisting of hydroxypropylmethylcellulose, hydroxypropylcellulose, hydroxyethylcellulose, methylcellulose, carboxymethylcellulose, polymeric polyethylene glycols and oxides, and polyoxypropylene-polyoxyethylene block copolymers.

6. An ophthalmic solution according to claim 5 having a viscosity within the range of from about 10 cps to about 150 cps at 23° C.

7. An ophthalmic solution according to claim 4 wherein said viscosity building agent is present in solution at a level of from about 0.05% to about 10% by weight.

8. An ophthalmic solution according to claims 1 or 2 or 3, which is adjusted to a pH of from about 4.5 to about 8.5.

9. A method of treating an eye condition characterized by abnormally structured tear films comprising topically applying to said eye a pharmacologically effective amount of the ophthalmic solution defined in claim 1.

* * * * *